(12) United States Patent
Song et al.

(10) Patent No.: US 9,243,268 B2
(45) Date of Patent: Jan. 26, 2016

(54) METHOD FOR PREPARING CYSTEINE OR A DERIVATIVE THEREOF USING A NOVEL O-PHOSPHOSERINE SULFHYDRYLASE

(71) Applicant: CJ CHEILJEDANG CORPORATION, Seoul (KR)

(72) Inventors: Byeong Cheol Song, Gyeonggi-do (KR); Jin Sook Chang, Seoul (KR); Jae Hyun Jo, Seoul (KR); Hye Won Kim, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 32 days.

(21) Appl. No.: 14/365,571

(22) PCT Filed: Dec. 14, 2012

(86) PCT No.: PCT/KR2012/010900
§ 371 (c)(1),
(2) Date: Jun. 13, 2014

(87) PCT Pub. No.: WO2013/089478
PCT Pub. Date: Jun. 20, 2013

(65) Prior Publication Data
US 2015/0004657 A1    Jan. 1, 2015

(30) Foreign Application Priority Data

Dec. 15, 2011 (KR) .......................... 10-2011-0135665

(51) Int. Cl.
*C12P 13/12* (2006.01)
*C12N 9/10* (2006.01)

(52) U.S. Cl.
CPC ............... *C12P 13/12* (2013.01); *C12N 9/1085* (2013.01); *C12Y 205/01065* (2013.01)

(58) Field of Classification Search
None
See application file for complete search history.

(56) References Cited

U.S. PATENT DOCUMENTS

| 6,579,705 B2 | 6/2003 | Maier et al. |
| 2007/0026505 A1 | 2/2007 | Madden et al. |
| 2009/0053778 A1 | 2/2009 | Sauer et al. |

FOREIGN PATENT DOCUMENTS

| EP | 0 272 365 A1 | 6/1988 |
| KR | 1020120041115 A | 4/2012 |
| WO | WO 2006/138689 A2 | 12/2006 |

OTHER PUBLICATIONS

Lucas et al., "Sequencing of the draft genome and assembly of Dethiobacter alkaliphilus AHT 1.," UniProt Consortium, Accession No. C0GC27, dated Dec. 14, 2011.
Lucas et al., "Sequence of the draft genome assembly of Dethiobacter alkaliphilus AHT 1," Genbank Accession No. EEG78762, dated Mar. 17, 2009.
Spring et al., "Complete genome sequence of Desulfotomaculum acetoxidans type strain (5575)," UniProt Consortium, Accession No. C8W164, dated Dec. 14, 2011.
Westrop et al., "Cysteine Biosynthesis in Trichomonas vaginalis Involves Cysteine Synthase Utilizing O-Phosphoserine," The Journal of Biochemistry 281 (35): 25062-25075, Sep. 1, 2006.
Agren et al., "The C-terminal of CysM from Mycobacterium tuberculosis protects the aminoacrylate intermediate and is involved in sulfur donor selectivity," FEBS Letters 583: 330-336, 2009.
Agren et al., "Cysteine Synthase (CysM) of Mycobacterium tuberculosis Is an O-Phosphoserine Sulfhydrylase. Evidence for an Alternative Cysteine Biosynthesis Pathway in Mycobacteria," The Journal of Biological Chemistry 283(46): 31567-31574, November.
Genbank Accession No. YP_003192083, accessed Apr. 29, 2010.
NCBI Reference Sequence Accession No. ZP_03728181, accessed Nov. 10, 2010.

*Primary Examiner* — Suzanne M Noakes
*Assistant Examiner* — Jae W Lee
(74) *Attorney, Agent, or Firm* — Cooley LLP (57) ABSTRACT

The present invention relates to a method for producing cysteine or derivatives thereof using novel O-phosphoserine sulfhydrylase. According to the present invention, a method for producing cysteine by novel O-phosphoserine sulfhydrylase (OPSS) using O-phosphoserine as a substrate is provided, and this method is advantageous in that cysteine can be simply and environmental-friendly produced in a high yield.

6 Claims, 4 Drawing Sheets

METHOD FOR PREPARING CYSTEINE OR A DERIVATIVE THEREOF USING A NOVEL O-PHOSPHOSERINE SULFHYDRYLASE

CROSS-REFERENCES TO RELATED APPLICATIONS

This application is a U.S. national phase application of International PCT Patent Application No. PCT/KR2012/010900, which was filed on Dec. 14, 2012, which claims priority to Korean Patent Application No. 10-2011-0135665, filed Dec. 15, 2011. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_030_00US_ST25.txt. The text file is 13 KB, was created on Jun. 13, 2014, and is being submitted electronically via EFS-Web.

TECHNICAL FIELD

The present invention relates to a method for producing cysteine or derivatives thereof using novel O-phosphoserine sulfhydrylase.

BACKGROUND ART

Cysteine is an important amino acid in sulfur metabolism of all living organisms. It is used in the biosynthesis of proteins, such as hair keratin, glutathione, biotin, methionine and other sulfur-containing metabolites, or used as a precursor of coenzyme A. In addition, the biosynthesis of cysteine is known to be closely associated with the biosynthesis of other amino acids like serine, glycine, and methionine. Industrially, cysteine and its derivatives are used in a various fields including the pharmaceutical industry (for treatment of bronchial diseases), the cosmetics industry (in hair shampoo, compositions for permanent waves), and the food industry (antioxidants, flavor enhancers, dough softeners).

Until now, cysteine has been produced chemically by acid hydrolysis of raw materials such as human hairs or animal feathers. However, not only a yield of the production of cysteine from hairs is as low as 7~8%, but also the use of hydrochloric acid or sulfuric acid cause a lot of waste resulting in environmental pollution. Further, the use of hairs as a raw material may induce the user to have a strong aversion thereto. These problems have caused a push for the development of environment-friendly production processes of cysteine. Therefore, a method of producing cysteine using microorganisms has been developed.

Representative microbial production of cysteine is 1) the biological conversion of D, L-ATC using a microorganism. This conversion process is, however, difficult to apply industrially due to the low solubility of the precursor D, L-ATC. 2) Another method of cysteine production is direct fermentation using *E. coli*. In this method, excessive accumulation of cysteine within microorganisms may incurs intracellular toxicity, and there's a limitation in the production of cysteine at a high concentration by using microorganism.

Referring to one of the biosynthesis pathways of cysteine in microorganisms and plants, O-acetyl-serine (OAS) acts as an intermediate precursor providing the carbon backbone of cysteine. O-acetylserine sulfhydrylase (OASS), using hydrogen sulfide as a sulfur donor, catalyses the conversion of OAS to cysteine. Therefore, cysteine can be produced from microorganisms accumulating OAS and various sulfur donors using OASS (U.S. Pat. No. 6,579,705).

The present inventors investigated a novel method for producing cysteine unlike the conventional method, and they discovered the existence of O-phosphoserine sulfhydrylase (OPSS) catalyzing synthesis of cysteine from O-phosphoserine (OPS) in a particular microorganism. OPS is an intermediate precursor of L-serine and has a shorter metabolic pathway than OAS. Thus, use of OPS can be advantageous, compared to use of OAS. In particular, it was found that OPSS derived from *Trichomonas vaginalis* does not require sulfer transferring coenzymes such as $mec^+$ and cys0, unlike OPSS derived from *Mycobacterium tuberculosis*, and also shows optimal activity at 37° C., unlike OPSS derived from *Aeropyrum pernix*.

DISCLOSURE

Technical Problem

The present inventors have made many efforts to develop a method for producing cysteine in a high yield, and as a result, they identified novel OPSS having an activity to synthesize cysteine using OPS as a substrate from various microorganisms, and found that this novel OPSS has higher cysteine-synthesizing activity than the known OPSS of *Trichomonas vaginalis*, thereby completing the present invention.

Technical Solution

An object of the present invention is to provide a method for producing cysteine or derivatives thereof comprising the step of reacting O-phosphoserine (OPS) with a sulfide in the presence of novel O-phosphoserine sulfhydrylase (OPSS) or a microorganism expressing the same, thereby producing cysteine or the derivatives thereof.

Advantageous Effects

The present invention provides a method for producing cysteine by novel O-phosphoserine sulfhydrylase (OPSS) using O-phosphoserine as a substrate, and this method is advantageous in that cysteine can be environment-friendly produced in a high yield by a simple method.

BEST MODE

In one aspect, the present invention provides a method for producing cysteine or derivatives thereof, comprising the step of reacting O-phosphoserine (OPS) with a sulfide in the presence of O-phosphoserine sulfhydrylase (OPSS) having an amino acid sequence represented by SEQ ID NO. 1 or 2, or a microorganism expressing the same, thereby producing cysteine or the derivatives thereof.

As used herein, the term "O-phosphoserine sulfhydrylase" (hereinafter, referred to as OPSS) refers to an enzyme that transfers a thiol group (SH group) to O-phosphoserine (hereinafter, referred to as OPS), converting OPS into cysteine.

In the present invention, OPSS may be represented by an amino acid sequence of SEQ ID NO. 1 or 2, that is a novel OPSS newly identified by the present inventors. Some modifications in the amino acid sequence represented by SEQ ID NO. 1 or 2 are possible, as long as it has an OPSS activity and maintains the activity. Those skilled in the art will readily understand that an amino acid sequence having 70% or higher, specifically 80% or higher, more specifically 90% or higher, and most specifically 95% or higher homology with the amino acid sequence by artificial modification is equivalent to the amino acid sequence of the present invention, as long as it has the desired activity.

Figure 1:
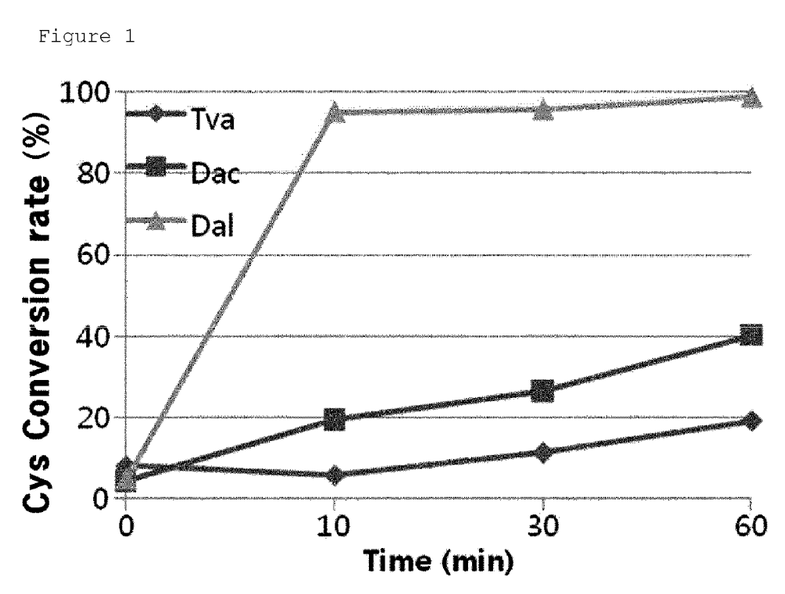
FIG. 1 shows the result of measuring cysteine conversion rates of three types of OPSSs at 10 minutes, 30 minutes, and 60 minutes.
Figure 3:
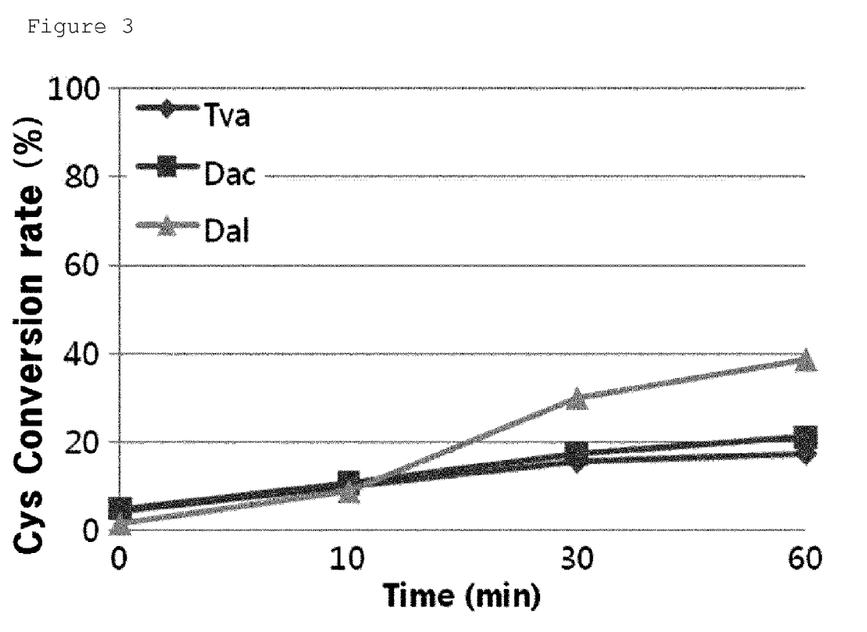
FIG. 3 shows the result of measuring cysteine conversion rates of three types of OPSSs at 10 minutes, 30 minutes, and 60 minutes using an OPS fermentation broth and sulfide as substrates.

In one specific embodiment of the present invention, Dac-OPSS having the amino acid sequence of SEQ ID NO. 1 and Dal-OPSS having the amino acid sequence of SEQ ID NO. 2 were used to evaluate their activities to synthesize cysteine by use of purified OPS or OPS fermentation broth as a substrate. As a result, they showed higher cysteine conversion rates than the control group, Tva-OPSS, so it was suggested that OPSS having the amino acid sequence of SEQ ID NO. 1 or 2 is able to produce cysteine in a high yield (FIGS. 1 and 3, and Tables 3 and 4).

As used herein, the term "homology" refers to a percentage of the sequence similarity between two polypeptide moieties. The correspondence between the sequences from one moiety to another can be determined by techniques known in the art. For example, homology can be determined by a direct comparison of the sequence information between two polypeptide molecules by aligning the sequence information and using readily available computer programs. Furthermore, homology can be determined by hybridization of polynucleotides under conditions that form stable duplexes between homologous regions, followed by disintegration with single-stranded-specific nuclease(s) and size determination of the disintegrated fragments.

As used herein, the term "sequence similarity" refers to the degree of coidentity or correspondence between nucleic acid or amino acid sequences of proteins that may or may not share a common evolutionary origin. In one specific embodiment, two amino acid sequences are "substantially homologous" or "substantially similar" when at least about 21% (specifically at least about 50%, and most specifically at least about 75%, 90%, 95%, 96%, 97%, or 99%) of the polypeptides match over the defined length of the amino acid sequences. Sequences that are substantially homologous can be identified by comparing the sequences using standard software available in sequence data banks, or in a hybridization experiment under, for example, stringent conditions as defined for that particular system. The defined appropriate hybridization conditions is within the skill of the art (see e.g., Sambrook et al., 1989, infra.).

As used herein, the term "cysteine conversion" is intended to refer to the catalytic reaction of OPSS which results in the conversion of the substrate OPS into the product cysteine, that is, it refers to the catalytic reaction of converting OPS into cysteine. Further, as used herein, the term "cysteine conversion rate" refers to the percentage of OPS converted into cysteine. Under optimal reaction conditions, 1 mole of OPS is converted into 1 mole of cysteine. For example, if 100 moles of OPS is converted into 100 moles of cysteine, the cysteine conversion rate is 100%. OPSS of the present invention catalyzes the conversion of OPS into cysteine, which shows a shorter metabolic pathway than the metabolic pathway using OAS, and thus it is advantageous in the production of precursors. Further, there is an advantage that OPSS of the present invention itself is able to produce cysteine without sulfur transferring coenzymes (mec$^+$ and cys0 of *M. tuberculosis*), unlike the conventional OPSS.

OPSS of the present invention may be encoded by a polynucleotide having a nucleotide sequence of SEQ ID NOs. 9 to 12. OPSS having the amino acid sequence of SEQ ID NO. 1 or 2 of the present invention may be encoded by a polynucleotide having the nucleotide sequence of SEQ ID NO. 9 or 10, respectively. More specifically, in order to increase heterogeneous protein expression in *E. coli*, it may be encoded by a polynucleotide having the nucleotide sequence of SEQ ID NO. 11 or 12 which is optimized for *E. coli* as optimizing codon usage.

The microorganism expressing OPSS of the present invention may be a microorganism which endogenously expresses OPSS of the present invention or a microorganism in which a nucleotide sequence encoding OPSS of the present invention is introduced in the form of a vector or integrated into the chromosome. The OPSS activity of the microorganism expressing OPSS may be further enhanced. A method of enhancing the OPSS activity includes a method of increasing the copy number by introducing a vector including a polynucleotide having the nucleotide sequence encoding OPSS into the microorganism, a method of optimizing codon usage of the nucleotide sequence according to codon usage favored by the microorganism, a method of substituting the promoter of the gene encoding OPSS with a strong promoter in the microorganism expressing OPSS, a method of introducing a mutation into the promoter, a method of introducing a mutation into the gene encoding the newly isolated OPSS to enhance the OPSS activity, or the like.

As used herein, the term "vector" refers to any vehicle for the cloning of and/or transferring a nucleic acid into a host cell. A vector may be a replicon which may be attached to other DNA segment so as to induce the replication of the attached segment. A "replicon" refers to any genetic element (e.g., plasmid, phage, cosmid, chromosome, virus) that functions as an autonomous unit of DNA replication in vivo, in other words, is able to replicate under its own control.

In the present invention, the microorganism expressing OPSS may be a microorganism that is obtained by transformation of the vector including OPSS. The transformation method may include any method to introduce the nucleic acid into cells, and may be carried out by selecting a suitable standard technique known in the art. For examples, it may include electroporation, calcium phosphate co-precipitation, retroviral infection, microinjection, DEAE-dextran, cationic liposome or the like, but is not limited thereto.

The microorganism expressing OPSS may be prokaryotic or eukaryotic, specifically, enterobacteria or coryneform bacteria, more specifically, a microorganism belonging to *Escherichia* sp., *Serratia* sp., or the like, and most specifically, *E. coli*.

OPSS can be isolated from a culture broth that is obtained by culturing the microorganism expressing the newly isolated OPSS in the present invention. Any method typically known in the art can be used, and in a specific embodiment of the present invention, a pET expression system manual (Novagen Inc.) was used to culture the microorganism, followed by isolation using Ni-NTA columns.

In the present invention, OPS used as a substrate of the novel OPSS may be an OPS fermentation broth prepared by fermentation as well as commercially available pure OPS. Example of the pure OPS may include product no. P0878 of Sigma-Aldrich or product no. CAS407-41-0 of Wako. Further, the OPS fermentation broth may be prepared by culturing a microorganism having OPS productivity, for example, microorganism deposited as no. KCCM 11103P (CA07-0022/pCL-prmf-serA*(G336V)-serC; see Korean Patent Publication No. 10-2012-0041115).

As used herein, the term "sulfide" refers to a compound of sulfur and more electropositive element than sulfur, and with respect to the object of the present invention, sulfide is used in the preparation of cysteine or derivatives thereof. The sulfide may be provided in solid form typically used in the art as well as in liquid form or gas form, due to the difference in pH, pressure, or solubility. So long as it may be converted to a thiol group (SH group), such as sulfide ($S^{2-}$), thiosulfate ($S_2O_3^{2-}$) etc., it is possible to use any sulfur compound. Specifically, $Na_2S$, $H_2S$, NaSH, $(NH_4)_2S$ and $S_2O_3$ may be used. In one specific embodiment of the present invention, $Na_2S$ was used as a sulfur source. The reaction of the present invention is a reaction of providing one thiol group to one reactive group of OPS in order to produce one cysteine or one cysteine derivative. In this reaction, sulfide may be specifically added at a molar concentration 0.1 to 3 times, and more specifically 1 to 2 times as high as that of OPS added, but is not limited thereto.

Optimization of the enzymatic conversion of OPS of the present invention may be achieved using various methods known in the art. For example, the optimization may be, but is not limited to, based on a full understanding of the characteristics of OPSS enzyme, specifically, the optimal temperature and pH, inhibition against substrates, substrate concentration, heat stability of OPSS enzyme itself, etc. In addition, the optimization may be determined by optimal conditions for the enzymatic conversion, in particular, the optimal OPSS concentration, the optimal balances of the used substrates concentrations, a preference for sulfide used in the enzymatic conversion except OPS substrate, a preference for buffers used in the conversion reaction, the influence of the generated ions, and presence of cofactors and their optimal concentrations, or etc.

Figure 4:
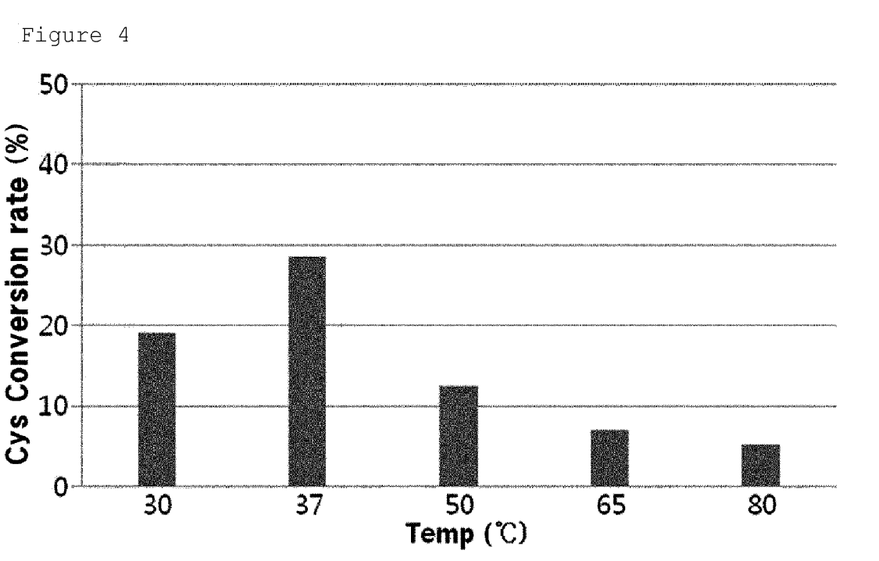
FIG. 4 shows the result of measuring cysteine conversion rates of Dal-OPSS according to temperature.

In one specific embodiment of the present invention, the cysteine conversion rate depending on pH and temperature was examined using Dal-OPSS. As a result, the optimal activity was observed at pH 7.0 to 7.4 (FIG. 2) and at a temperature of 37° C. (FIG. 4).

In the present invention, additional cofactors for cysteine conversion reaction may be added, for example, PLP (pyridoxal-5'-phosphate), DTT (dithiothreitol), or PLP and DTT. These cofactors are able to improve the efficiency of cysteine conversion reaction. In a specific embodiment of the present invention, it was confirmed that addition of 0.2 mM PLP, 25 mM DTT, or both of the two cofactors increased the cysteine conversion rate (Table 5). PLP may be, but is not limited to, specifically added 0.001 to 2 mM, and more specifically 0.01 to 1 mM. Further, DTT may be, but is not limited to, specifically added 0.001 to 100 mM, and more specifically 0.01 to 50 mM.

The method of the present invention may further include the step of isolating and purifying the cysteine or derivatives thereof produced in the reaction step. In this step, the desired cysteine can be collected by isolating and purifying the cysteine from a reaction mixture using a suitable method known in the art.

Those skilled in the art may readily synthesize cysteine derivatives using the known chemical synthetic method from cysteine prepared by the method of the present invention. Cysteine may be readily reacted with an acetylation agent to synthesize NAC (N-acetylcysteine) and with haloacetic acid under basic conditions to synthesize SCMC (S-carboxymethylcysteine). These cysteine derivatives are used as pharmaceutical materials that treat coughs, bronchitis, bronchial asthma, sore throat or etc.

Mode for Invention

Hereinafter, the present invention will be described in more detail with reference to Examples. However, these Examples are for illustrative purposes only, and the invention is not intended to be limited by these Examples.

EXAMPLE 1

Identification of O-Phosphoserine Sulfhydrylase (OPSS) Enzyme

It was reported that *Trichomonas vaginalis*-derived OPSS has an activity without cofactors, unlike *Mycobacterium tuberculosis*-derived OPSS which requires two types of cofactors in addition to OPSS, and has an optical activity at 37° C., unlike *Aeropyrum pernix*-derived OPSS which exhibits an optical activity at 60° C. Based on this fact, the present inventors isolated novel OPSSs derived from microorganisms, which show high sequence homology of the OPSS amino acid sequence derived form *T. vaginalis*. The novel OPSSs have an amino acid sequence of SEQ ID NO. 1 or 2, and is designated as Dac-OPSS or Dal-OPSS, respectively. Further, the novel OPSS having the amino acid sequence of SEQ ID NO. 1 or 2 is encoded by a polynucleotide having a nucleotide sequence of SEQ ID NO. 9 or 10, respectively.

Because these two OPSSs are not derived from *E. coli*, their expression in *E. coli* may be difficult. To facilitate their expression in *E. coli*, codon optimization of the newly isolated OPSSs was carried out using Jcat which is a tool for codon usage optimization (www.jcat.de). Through this procedure, codon usage optimization of the polynucleotides of SEQ ID NOs. 9 and 10 was carried out to give SEQ ID NOs. 11 and 12. The polynucleotides having the nucleotide sequences of SEQ ID NOs. 11 and 12 were provided for and synthesized by Genotech Corp., and they were received in the form of vectors by Topo TA cloning. In order to obtain the OPSS enzyme from each strain, a pET28a (novagen) vector system, typically used for enzyme expression, was constructed.

The 3 types of OPSS enzymes-expressing vectors and templates and primers used for the construction of the vectors are the same as shown in the following Table 1. PCR was carried out using combinations of the templates and primers to amplify each of the OPSS genes. The resulting gene fragments and the vector pET28a were treated with restriction enzymes, NdeI and HindIII (at 37° C. for 3 hours). Thereafter, each gene fragment was inserted into the pET28a vector by a typical ligation method. The enzyme-expressing vectors and the gene sequences thereof were examined by sequencing. The enzyme-expressing vectors prepared were introduced into *E. coli* having the genotype of DE3 so as to prepare three types of OPSS enzyme-expressing strains.

TABLE 1

| Name of enzyme | Name of vector | Template used | Primer used |
|---|---|---|---|
| Tva-OPSS | pET28a-Tva-OPSS | Synthetic DNA | SEQ ID NOs. 3(F) and 4 (R) |
| Dac-OPSS | pET28a-Dac-OPSS | Synthetic DNA | SEQ ID NOs. 5(F) and 6(R) |
| Dal-OPSS | pET28a-Dal-OPSS | Synthetic DNA | SEQ ID NOs. 7(F) and 8(R) |

The enzyme expression was carried out with reference to the pET system manual (novagen). Single colonies of each strain were selected from LB plate, and inoculated in 5 ml of LB liquid media, followed by culture at 37° C. and 200 rpm for 16 hours. The strains were re-inoculated in 25 ml of fresh LB liquid media (flasks of 250 ml volume) and cultured until $OD_{600}$ reached 0.5~0.6 (2~3 hours) under the same culture conditions. Then, 1 mM IPTG was added to the media, followed by culture at 18° C. and 120 rpm for 18 hours for induction of the enzyme expression. Purification of the enzymes was performed using his-tag and Ni-NTA columns. The purification was performed using His spintrap (GE healthcare).

EXAMPLE 2

Assay of OPSS Enzyme for Cysteine Synthesis Activity

The cysteine converting activities of above obtained 3 types of OPSS enzymes were measured to examine whether cysteine can be synthesized by using OPS as a substrate. The conditions and methods for assay of cystein converting activity (cysM enzyme assay), was made reference to previous reports (Mino K and Ishikawa K, FEBS letters, 551: 133-138, 2003; Burns K E, Baumgart S, Dorrestein P C, Zhai H, McLafferty F W and Begley T P, J. Am. Chem. Soc., 127: 11602-11603, 2005; Westrop G D, Goodall G, Mottram J C and Coombs G H, J. Biol. Chem., 281: 25062-25075, 2006). Assay conditions for enzyme activity are the same as shown in Table 2, below.

TABLE 2

| Stock sol'n | Final Conc. | | Blank | OBSS |
|---|---|---|---|---|
| 6xhis-enzyme | — | | — | 40 (50 µg) |
| 1 M HEPES (pH 7.4) | 100 | mM HEPES | 100 | 100 |
| 0.5 M Na₂S | 10 | mM Na₂S | 20 | 20 |
| 10 mM PLP | 0.2 | mM PLP | 20 | 20 |
| 100 mM OPS | 5 | mM OPS | 0 | 50 |
| DW | | | 790 | 750 |
| Total | | | 1000 | 1000 |

Reaction solutions, except the enzymes, were incubated at 37° C. for 5 min. After then, 50 µg of purified OPSS was added to the reaction solution, cultured at 37° C. 100 mL of the enzyme reaction solutions were taken after 10 min, 30 min, 60 min, and mixed with 100 mL of 33.2% TCA to stop the enzymatic reaction. The cysteine concentrations in the enzyme reaction solution were quantified by measuring absorbance at $OD_{560}$ according to the Gaitonde method. Cysteine synthesis activities of the three different OPSSs are shown in FIG. 1 and the following Table 3. The cysteine synthesis titers of the OPSSs were assayed by comparing cysteine conversion rates over reaction time.

TABLE 3

| | Cysteine conversion rate (%) | | |
|---|---|---|---|
| | 10 minutes | 30 minutes | 60 minutes |
| Tva-OPSS | 5.94 | 11.48 | 19.32 |
| Dac-OPSS | 19.47 | 26.47 | 40.26 |
| Dal-OPSS | 94.98 | 95.52 | 98.65 |

The above results showed that Tva-OPSS has an activity to synthesize cysteine using OPS as a substrate, and cysteine synthesis activities of the novel OPSSs, Dac-OPSS and Dal-OPSS, were discovered for the first time. Compared to Tva-OPSS, Dac-OPSS and Dal-OPSS were found to increase cysteine conversion rates, and in particular, Dal-OPSS was found to have remarkably high activity.

EXAMPLE 3 pH Sensitivity of OPSS Enzyme

Figure 2:
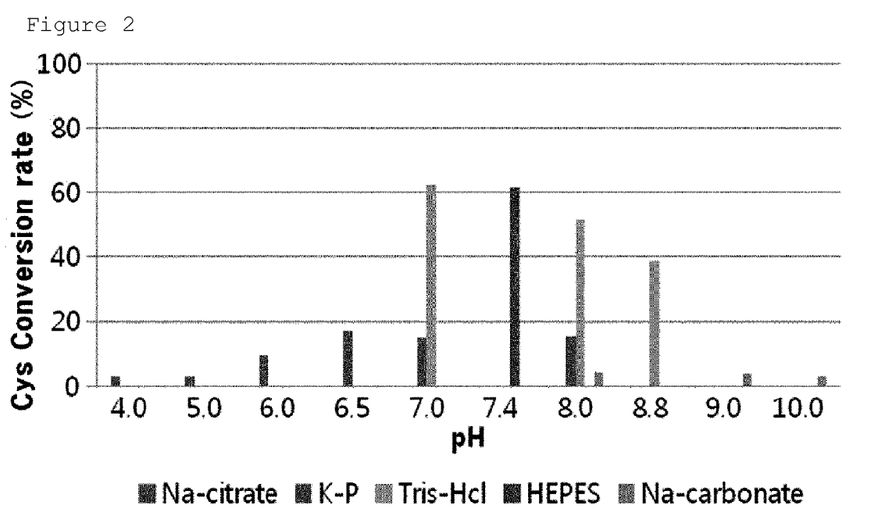
FIG. 2 shows the result of measuring cysteine conversion rates according to pH to examine pH sensitivity of Dal-OPSS.

In order to examine the effect of pH on the cysteine synthesis, the cysteine conversion rates of Dal-OPSS according to pH were measured. In 100 mM of buffer, 50 µg/mL thereof was subjected to reaction at 37° C. for 30 minutes. In this regard, K-phosphate buffer with pH of 6.4/7.0/7.4/8.0, Tris-HCl buffer with pH of 7.0/7.4/8.0/8.5/8.8, Na-carbonate buffer with pH of 8.0/8.5/9.0/10.0, HEPES buffer with pH of 7.4, and Na-citrate buffer with pH of 4.0/5.0/6.0 were used. The quantitative analysis of the produced cysteine was carried out using the Gaitonde method. As shown in FIG. 2, the highest activity was observed at pH 7.0~7.4, and the highest activity was detected in Tris-HCl (pH 7.0), and little activity was detected in Na-citrate and Na-carbonate buffers. Further, an optimal pH differed from one buffer to another.

EXAMPLE 4

Cysteine Conversion Reaction of OPSS Enzyme with Use of OPS Fermentation Broth as Substrate KCCM 11103P (CA07-0022/pCL-prmf-serA*(G336V)-serC; Korean Patent Publication No. 10-2012-0041115) having OPS productivity, which was prepared by introducing serB deletion and mutated serA* into the E. coli strain W3110, were plated on MMYE solid media and cultured at 30° C. overnight. A platinum loop of the strain cultured on MMYE solid media overnight was inoculated in 25 ml of titer medium and then cultured in a 30° C. incubator at 200 rpm for 48 hours. The cysteine conversion rates of Tva-OPSS, Dac-OPSS and Dal-OPSS were examined using the OPS fermentation broth prepared as a substrate. Cysteine conversion reaction was performed in the presence of 5.4 mM OPS fermentation broth, 10 mM Na₂S, and 0.2 mM PLP at each OPSS concentration of 50 µg/ml at 37° C. The amounts of the produced cysteine were measured using the Gaitonde method. FIG. 3 and Table 4 show cysteine conversion rates of three types of OPSSs at 37° C. over time. Among the three types of OPSSs, Dal-OPSS was found to show the highest conversion rate under the above conversion reaction conditions.

TABLE 4

| | Cysteine conversion rate (%) | | |
|---|---|---|---|
| | 10 minutes | 30 minutes | 60 minutes |
| Tva-OPSS | 10.23 | 15.62 | 17.44 |
| Dac-OPSS | 10.87 | 17.43 | 21.11 |
| Dal-OPSS | 8.93 | 29.88 | 38.64 |

Meanwhile, in order to examine the effect of temperature on the cysteine synthesis, the cysteine conversion rates of Dal-OPSS according to temperature were measured. The cysteine conversion rates were measured under the same conditions as above, except for varying the temperature at 30° C., 37° C., 50° C., 65° C. and 80° C. As a result, as shown in FIG. 4, when Dal-OPSS was reacted at each temperature for 30 minutes, it showed the highest activity at 37° C.

EXAMPLE 5

Cofactor Requirement of OPSS

In order to examine cofactor requirements in the cysteine conversion reaction, the cysteine conversion rate of Dal-OPSS was measured in the absence or presence of PLP (pyridoxal-5'-phosphate) and DTT (dithiothreitol). In this regard, 5.4 mM OPS fermentation broth and 10 mM $Na_2S$ as the substrates were reacted at 37° C. for 30 minutes in the presence of 25 mM DTT and/or 0.2 mM PLP. The cysteine produced was quantified using the Gaitonde method. The results are shown in Table 5, below.

TABLE 5

| Dal-OPSS | Cysteine conversion rate (%) |
|---|---|
| (−) PLP, (−) DTT | 12.88 |
| (+) PLP, (−) DTT | 20.15 |
| (−) PLP, (+) DTT | 24.32 |
| (+) PLP, (+) DTT | 31.54 |

As shown in Table 5, the cysteine conversion rate of an experimental group to which both PLP and DTT were added was about 2.4 times as high as that of the control group to which both PLP and DTT were not added. Further, the cysteine conversion rate was also increased in an experimental group which PLP or DTT was added to respectively. Thus, both PLP and DTT were observed to have a positive influence on the cysteine conversion.

The invention claimed is:

1. A method for producing cysteine or derivatives thereof, comprising the step of reacting O-phosphoserine (OPS) with a sulfide in the presence of O-phosphoserine sulfhydrylase (OPSS) having an amino acid sequence represented by SEQ ID NO: 1 or 2, or a microorganism expressing the same, thereby producing cysteine or the derivatives thereof, wherein said method further comprises the step of separating and purifying the cysteine or derivatives thereof.

2. The method according to claim 1, wherein the OPSS is encoded by a polynucleotide having a nucleotide sequence selected from the group consisting of SEQ ID NO: 9 to 12.

3. The method according to claim 1, wherein the OPS is purified OPS or a fermentation broth of a microorganism including OPS.

4. The method according to claim 1, wherein the sulfide is selected from the group consisting of $Na_2S$, $H_2S$, NaSH, $(NH_4)_2S$ and $S_2O_3$.

5. The method according to claim 1, wherein the sulfide is added at a molar concentration which is 0.1 to 3 times as high as that of OPS added in the reaction.

6. The method according to claim 1, wherein a cofactor during the reaction is further added as 0.001 to 2 mM pyridoxal-5'-phosphate (PLP) or 0.001 to 100 mM dithiothreitol (DTT).

* * * * *

SEQUENCE LISTING

```
<160> NUMBER OF SEQ ID NOS: 12

<210> SEQ ID NO 1
<211> LENGTH: 318
<212> TYPE: PRT
<213> ORGANISM: Artificial Sequence
<220> FEATURE:
<223> OTHER INFORMATION: Dac-OPSS

<400> SEQUENCE: 1

Met Ile Cys Asp Asn Ile Leu Lys Thr Ile Cys Asn Thr Pro Met Ile
1               5                   10                  15

Arg Ile Asn Arg Leu Asn Pro Asn Pro Asn Val Glu Ile Tyr Ala Lys
            20                  25                  30

Phe Glu Gly Thr Asn Pro Gly Gly Ser Ile Lys Asp Arg Ile Ala Leu
        35                  40                  45

Lys Met Ile Glu Gln Ala Glu Ala Glu Gly Val Leu Asn Arg Lys Lys
    50                  55                  60

Thr Ile Ile Glu Ala Thr Ser Gly Asn Thr Gly Ile Ala Leu Ala Met
65                  70                  75                  80

Ile Gly Ala Val Lys Asp Tyr Lys Val Glu Ile Val Met Ser Glu Ala
                85                  90                  95

Val Ser Ile Glu Arg Arg Lys Met Ile Gln Ala Phe Gly Ala Lys Val
            100                 105                 110

Ile Leu Thr Asp Pro Glu Phe Gly Thr Asp Gly Ala Ile Leu Lys Val
        115                 120                 125

Arg Lys Leu Leu Glu Gln Tyr Pro Asp Arg Tyr Phe Cys Thr Asp Gln
    130                 135                 140

Phe Thr Asn Lys Tyr Asn Lys Leu Ala His Ser Glu Ile Thr Ala Glu
145                 150                 155                 160

Glu Ile Trp Phe Gln Thr Asn Gly Arg Val Asp Tyr Phe Val Ser Gly
                165                 170                 175

Leu Gly Thr Ser Gly Thr Leu Met Gly Val Gly Ala Gly Leu Lys Lys
            180                 185                 190
```

Tyr Asn Pro Lys Ile Lys Ile Ile Ser Ala Glu Pro Val Ala Gly His
            195                 200                 205

Tyr Ile Gln Gly Leu Lys Asn Leu Gln Glu Ala Ile Val Pro Gly Ile
    210                 215                 220

Tyr Asn Glu Ala Glu Leu Asp Glu Ile Ile Met Ile Glu Thr Glu Glu
225                 230                 235                 240

Ala Phe Glu Met Ala Arg Gln Ile Val Arg Lys Gly Ile Phe Val
                245                 250                 255

Gly Met Ser Ser Gly Ala Ser Met Leu Gly Ala Val Lys Ile Ala Arg
            260                 265                 270

Lys Leu Ser Ser Gly Val Ile Val Thr Ile Phe Pro Asp Arg Gly Glu
        275                 280                 285

Lys Tyr Leu Ser Thr Asp Leu Phe Lys Ser Glu Ala Gly Asp Gly Lys
        290                 295                 300

Leu Gly Arg Met Glu Ala Asp Arg Phe Cys Arg Lys Tyr Lys
305                 310                 315

<210> SEQ ID NO 2
<211> LENGTH: 314
<212> TYPE: PRT
<213> ORGANISM: Artificial Sequence
<220> FEATURE:
<223> OTHER INFORMATION: Dal-OPSS

<400> SEQUENCE: 2

Met Lys Ala Asn Ile Leu Glu Ala Ile Gly Glu Thr Pro Leu Val Arg
  1               5                  10                  15

Ile Asn Arg Leu His Thr Asn Pro Gln Val Thr Leu Ala Val Lys Leu
             20                  25                  30

Glu Gly Asn Asn Pro Gly Gly Ser Val Lys Asp Arg Ile Ala Tyr Tyr
         35                  40                  45

Met Leu Arg Lys Ala Glu Glu Lys Gly Glu Leu Thr Lys Asn Lys Ile
     50                  55                  60

Ile Leu Glu Pro Thr Ser Gly Asn Thr Gly Ile Gly Leu Ala Met Ala
 65                  70                  75                  80

Ala Ser Val Met Gly Tyr Arg Leu Val Val Thr Met Ser Glu Lys Met
                 85                  90                  95

Ser Ser Glu Arg Arg Lys Met Leu Glu Val Phe Gly Ala Glu Leu Val
            100                 105                 110

Leu Thr Pro Gly Glu Leu Gly Thr Asp Gly Ala Ile Met Lys Ala Arg
        115                 120                 125

Glu Met Ile Ala Lys Asp Pro Asp Arg Tyr Tyr Met Pro Asn Gln Phe
    130                 135                 140

Ala Asn Glu Asn Asn Tyr Met Val His Tyr Glu Thr Thr Ala Glu Glu
145                 150                 155                 160

Ile Trp Arg Gln Thr Asp Asn Lys Val Thr His Phe Val Ala Gly Met
                165                 170                 175

Gly Thr Thr Gly Thr Leu Met Gly Ala Ser Arg Arg Leu Lys Glu Leu
            180                 185                 190

Asn Pro Asp Ile Lys Ile Ile Gly Val Glu Pro Tyr Met Asn His Lys
        195                 200                 205

Ile Gln Gly Leu Lys Asn Met Glu Glu Ala Ile Lys Pro Ala Ile Tyr
    210                 215                 220

Asp Ser Lys Arg Leu Asp Glu Lys Ile Asn Val Ser Asp Glu Asp Ala
225                 230                 235                 240

Phe Glu Met Ala Phe Arg Leu Thr Arg Glu Glu Gly Ile Phe Ala Gly
                245                 250                 255

Ile Ser Ala Gly Ala Ala Met His Ala Ala Ile Ser Val Ala Asn Lys
            260                 265                 270

Leu Thr Ser Gly Phe Val Val Ala Ile Ile Pro Asp Arg Gly Asp Lys
        275                 280                 285

Tyr Met Ser Thr Asp Leu Phe Cys Ala Glu Cys Lys Arg Arg Arg
    290                 295                 300

Pro Asp Cys Leu Leu Thr Glu Asn Leu Phe
305                 310

<210> SEQ ID NO 3
<211> LENGTH: 27
<212> TYPE: DNA
<213> ORGANISM: Artificial Sequence
<220> FEATURE:
<223> OTHER INFORMATION: forward primer for Tva-OPSS

<400> SEQUENCE: 3
gctcatatgt tattttagcg atctcta                                       27

<210> SEQ ID NO 4
<211> LENGTH: 30
<212> TYPE: DNA
<213> ORGANISM: Artificial Sequence
<220> FEATURE:
<223> OTHER INFORMATION: reverse primer for Tva-OPSS

<400> SEQUENCE: 4
gtaggatcca agtgcagatt cgaacaattt                                    30

<210> SEQ ID NO 5
<211> LENGTH: 27
<212> TYPE: DNA
<213> ORGANISM: Artificial Sequence
<220> FEATURE:
<223> OTHER INFORMATION: forward primer for Dac-OPSS

<400> SEQUENCE: 5
gctcatatga tctgcgacaa catcctg                                       27

<210> SEQ ID NO 6
<211> LENGTH: 35
<212> TYPE: DNA
<213> ORGANISM: Artificial Sequence
<220> FEATURE:
<223> OTHER INFORMATION: reverse primer for Dac-OPSS

<400> SEQUENCE: 6
gtaggatcct tatttgtatt tacggcagaa acggt                              35

<210> SEQ ID NO 7
<211> LENGTH: 30
<212> TYPE: DNA
<213> ORGANISM: Artificial Sequence
<220> FEATURE:
<223> OTHER INFORMATION: forward primer for Dal-OPSS

<400> SEQUENCE: 7
gctcatatga aagctaacat cctggaagct                                    30

<210> SEQ ID NO 8
<211> LENGTH: 32
<212> TYPE: DNA

```
<213> ORGANISM: Artificial Sequence
<220> FEATURE:
<223> OTHER INFORMATION: reverse primer for Dal-OPSS

<400> SEQUENCE: 8
gtactcgagt tagaacaggt tttcggtcag ca                                32

<210> SEQ ID NO 9
<211> LENGTH: 957
<212> TYPE: DNA
<213> ORGANISM: Artificial Sequence
<220> FEATURE:
<223> OTHER INFORMATION: Dac-OPSS

<400> SEQUENCE: 9
atgatttgcg ataatatact caagaccata tgcaatacgc cgatgatcag aattaatcgg    60
ctgaatccaa acccaaatgt ggagatctat gcaaaatttg aaggcacaaa tcccggagga   120
agcataaaag atcggattgc gcttaagatg atcgagcagg ccgaggccga aggtgtactt   180
aacaggaaaa aaaccatcat agaggcaact tctggcaata caggcattgc gctggcgatg   240
atcggagcgg tcaaggacta caaggtggaa attgttatga gtgaagccgt atcgatcgaa   300
aggcgcaaga tgatacaggc attcggcgcg aaggtcatcc tgaccgatcc ggaatttgga   360
acggacggtg ctattcttaa agtacgcaag ttgctggagc aatatccgga tcgctatttc   420
tgcacagatc agttcacgaa taagtacaat aaactcgccc atagtgaaat tactgccgaa   480
gagatctggt tccaaacgaa tggcagagtt gattatttcg tttcagggtt gggaacatcg   540
ggaaccttga tgggggttgg tgccggcctg aaaaagtaca atcctaaaat aaaaatcatc   600
agtgcggaac cggttgccgg gcattatatt cagggtctga aaaatcttca ggaagcgatt   660
gttccgggca tttataatga agctgaactg gatgaaatta ttatgatcga aactgaggaa   720
gccttcgaga tggcccgtca gattgtccgc aaggaaggga tctttgtcgg catgagcagt   780
ggtgcgtcca tgttaggagc ggttaaaatt gcccgcaagc tttcttcagg tgtaattgtt   840 actattttc ctgatcgtgg agaaaaatat ttaagcacgg atctcttcaa gtctgaggca   900
ggtgatggaa aattaggacg gatggaggca gacagatttt gccgcaaata caaataa     957

<210> SEQ ID NO 10
<211> LENGTH: 945
<212> TYPE: DNA
<213> ORGANISM: Artificial Sequence
<220> FEATURE:
<223> OTHER INFORMATION: Dal-OPSS

<400> SEQUENCE: 10
atgaaagcta atattctgga agccattggc gaaacgcctt tggtacgaat caatcgttta    60
cataccaatc cacaggttac cctggctgta agctggagg gcaacaatcc gggcggaagt   120
gttaaggacc ggattgccta ctacatgctg cgaaaagctg aagaaaaagg tgaactgacc   180
aaaaataaaa ttatcctgga gcccaccagc ggcaacaccg catcggcct  ggccatggct   240 gcctcggtga tgggctatcg cctggtggtg accatgtctg aaaagatgag cagtgagcga   300
cgcaaaatgc tggaggtgtt tggcgccgaa ttagtactga ctccaggcga gttgggcacc   360
gatggtgcca ttatgaaggc ccgggaaatg atagccaagg acccggaccg ctactatatg   420
cctaaccaat ttgccaatga aacaactat atggtacact atgaaacaac cgctgaagaa   480
atctggcgac aaaccgataa taaggtaaca cactttgtgg ccggtatggg gaccaccggc   540
acattaatgg gcgcttctag acgcctcaaa gaactgaatc ccgacattaa gattatcggt   600
```

```
gtagagcctt atatgaacca taaaatccag ggactcaaga acatggaaga ggccattaaa    660
ccggccatat atgattccaa acgactggat gaaaaaataa atgtcagcga tgaagatgct    720
tttgaaatgg ccttccgtct cacccgggaa gaaggaatct tgccggaat ttctgcagga     780 gcagccatgc atgcagcaat cagtgtggcc aataaactca cctcaggctt tgtggttgcc    840
attattccag accgcggtga taagtatatg tccaccgatt tattctgtgc tgaacgttgc    900
aaaaggcgca gacccgactg cctgttgacg gagaatctct tttaa                   945
```

```
<210> SEQ ID NO 11
<211> LENGTH: 957
<212> TYPE: DNA
<213> ORGANISM: Artificial Sequence
<220> FEATURE:
<223> OTHER INFORMATION: Dac-OPSS codon usage optimize

<400> SEQUENCE: 11
atgatctgcg acaacatcct gaaaaccatc tgcaacaccc cgatgatccg tatcaaccgt     60
ctgaacccga acccgaacgt tgaaatctac gctaaattcg aaggtaccaa cccgggtggt    120
tctatcaaag accgtatcgc tctgaaaatg atcgaacagg ctgaagctga aggtgttctg    180
aaccgtaaaa aaaccatcat cgaagctacc tctggtaaca ccggtatcgc tctggctatg    240
atcggtgctg ttaaagacta caagttgaa atcgttatgt ctgaagctgt ttctatcgaa     300
cgtcgtaaaa tgatccaggc tttcggtgct aaagttatcc tgaccgaccc ggaattcggt    360
accgacggtg ctatcctgaa agttcgtaaa ctgctggaac agtacccgga ccgttacttc    420
tgcaccgacc agttcaccaa caaatacaac aaactggctc actctgaaat caccgctgaa    480
gaaatctggt tccagaccaa cggtcgtgtt gactacttcg tttctggtct gggtacctct    540
ggtacgctga tgggtgttgg tgctggtctg aaaaaataca cccgaaaat caaaatcatc     600 tctgctgaac cggttgctgg tcactacatc cagggtctga aaacctgca ggaagctatc     660 gttccgggta tctacaacga agctgaactg gacgaaatca tcatgatcga aaccgaagaa    720
gctttcgaaa tggctcgtca gatcgttcgt aaagaaggta tcttcgttgg tatgtcttct    780
ggtgcttcta tgctgggtgc tgttaaaatc gctcgtaaac tgtcttctgg tgttatcgtt    840
accatcttcc cggaccgtgg tgaaaaatac ctgtctaccg acctgttcaa atctgaagct    900
ggtgacggta aactgggtcg tatggaagct gaccgtttct gccgtaaata caaataa      957
```

```
<210> SEQ ID NO 12
<211> LENGTH: 945
<212> TYPE: DNA
<213> ORGANISM: Artificial Sequence
<220> FEATURE:
<223> OTHER INFORMATION: Dal-OPSS codon usage optimize

<400> SEQUENCE: 12
atgaaagcta acatcctgga agctatcggt gaaaccccgc tggttcgtat caaccgtctg     60
cacaccaacc cgcaggttac cctggctgtt aaactggaag gtaacaaccc gggtggttct    120
gttaaagacc gtatcgctta ctacatgctg cgtaaagctg aagaaaaagg tgaactgacc    180
aaaaacaaaa tcatcctgga accgacctct ggtaacaccg gtatcggtct ggctatggct    240
gcttctgtta tgggttaccg tctggttgtt accatgtctg aaaaaatgtc ttctgaacgt    300
cgtaaaatgc tggaagtttt cggtgctgaa ctggttctga ccccgggtga actgggtacc    360
gacggtgcta tcatgaaagc tcgtgaaatg atcgctaaag cccggaccg ttactacatg    420
```

```
ccgaaccagt tcgctaacga aaacaactac atggttcact acgaaaccac cgctgaagaa    480
atctggcgtc agaccgacaa caaagttacc cacttcgttg ctggtatggg taccaccggt    540
accctgatgg gtgcttctcg tcgtctgaaa gaactgaacc cggacatcaa aatcatcggt    600
gttgaaccgt acatgaacca caaaatccag ggtctgaaaa acatggaaga agctatcaaa    660
ccggctatct acgactctaa acgtctggac gaaaaaatca acgtttctga cgaagacgct    720
ttcgaaatgg ctttccgtct gacccgtgaa gaaggtatct tcgctggtat ctctgctggt    780
gctgctatgc acgctgctat ctctgttgct aacaaactga cctctggttt cgttgttgct    840
atcatcccgg accgtggtga caaatacatg tctaccgacc tgttctgcgc tgaacgttgc    900
aaacgtcgtc gtccggactg cctgctgacc gaaaacctgt tctaa                   945
```